United States Patent
Fisk

(10) Patent No.: US 8,567,252 B2
(45) Date of Patent: Oct. 29, 2013

(54) AUTOMATIC SONIC/ULTRASONIC DATA ACQUISITION DEVICE AND SYSTEM

(76) Inventor: Paul Fisk, Princeton, MA (US)

(*) Notice: Subject to any disclaimer, the term of this patent is extended or adjusted under 35 U.S.C. 154(b) by 252 days.

(21) Appl. No.: 12/958,535

(22) Filed: Dec. 2, 2010

(65) Prior Publication Data

US 2011/0154902 A1 Jun. 30, 2011

Related U.S. Application Data

(60) Provisional application No. 61/266,246, filed on Dec. 3, 2009.

(51) Int. Cl.
*G01N 29/265* (2006.01)
*G01N 33/38* (2006.01)

(52) U.S. Cl.
USPC ............................................ 73/639; 73/12.11

(58) Field of Classification Search
USPC .............. 73/639, 635, 597–598, 12.01, 12.11
See application file for complete search history.

(56) References Cited

U.S. PATENT DOCUMENTS

| | | | | |
|---|---|---|---|---|
| 3,999,423 A * | 12/1976 | Tyree | ............................... | 73/635 |
| 4,055,990 A * | 11/1977 | Topping | ........................... | 73/623 |
| 4,163,393 A * | 8/1979 | Gutierrez et al. | ................ | 73/584 |
| 4,898,034 A * | 2/1990 | Kupperman et al. | ............ | 73/644 |
| 5,404,755 A * | 4/1995 | Olson et al. | ...................... | 73/639 |
| 5,996,413 A | 12/1999 | Iyer et al. | | |
| 6,105,430 A | 8/2000 | Kepler et al. | | |
| 6,536,553 B1 * | 3/2003 | Scanlon | ......................... | 181/108 |
| 6,581,466 B1 * | 6/2003 | Costley et al. | ................... | 73/584 |

* cited by examiner

*Primary Examiner* — Peter Macchiarolo
*Assistant Examiner* — Rose M Miller
(74) *Attorney, Agent, or Firm* — Brian M. Dingman; Dingman IP Law, PC

(57) ABSTRACT

An automatic sonic/ultrasonic data acquisition device that is constructed and arranged to be moved across the surface of a concrete structure, to collect data from the structure. There is a frame, a number of wheels carried by the frame, one or more sensors carried by a wheel and constructed and arranged to contact the structure as the wheels roll along a surface of the structure, and an energy source for initiating compressional and/or shear waves in the structure that are sensed by the sensors. The wheels rotate properly timed and in unison so that the pressure transducers are in contact with the surface when the sound waves are initiated.

9 Claims, 7 Drawing Sheets

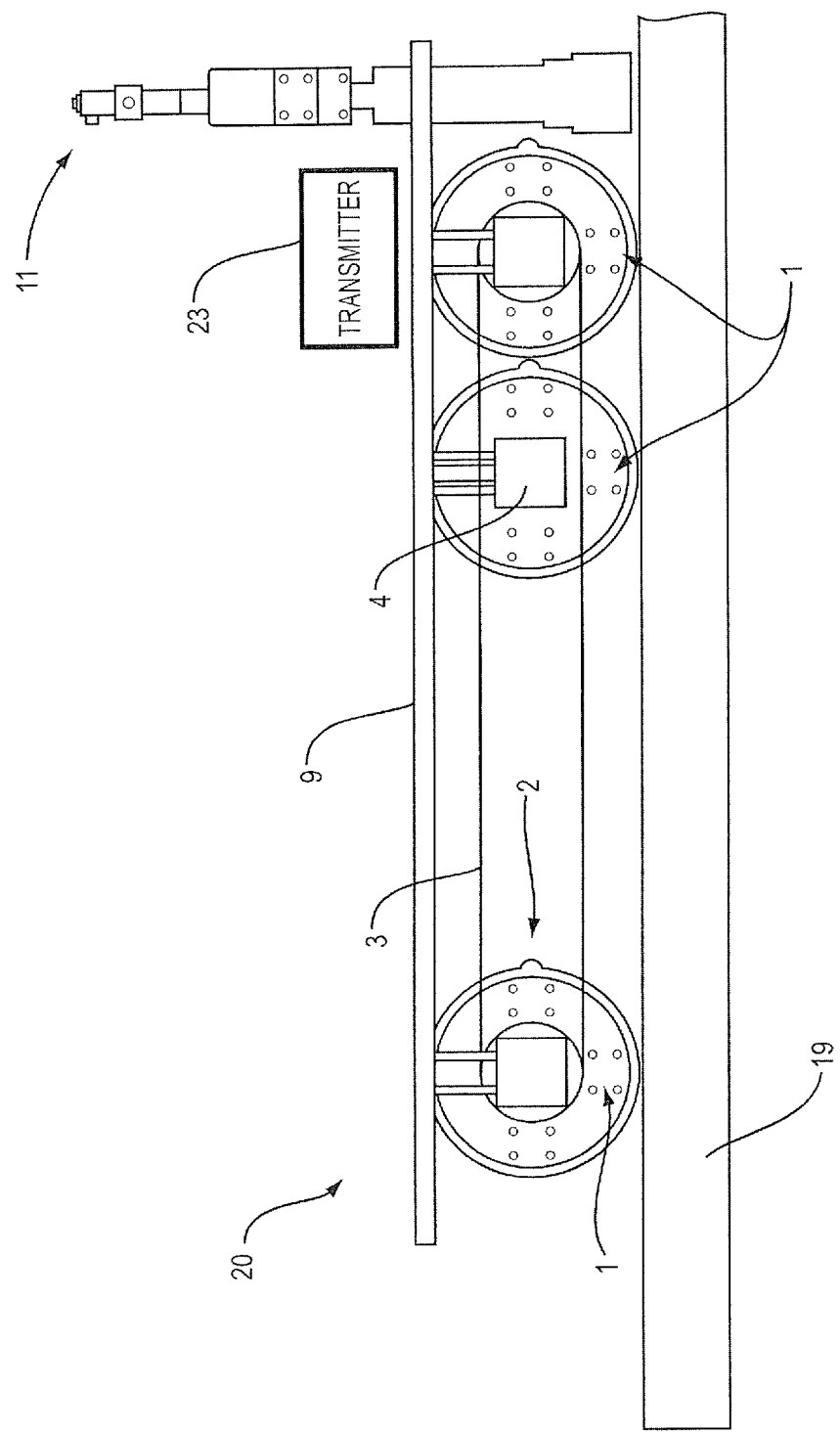

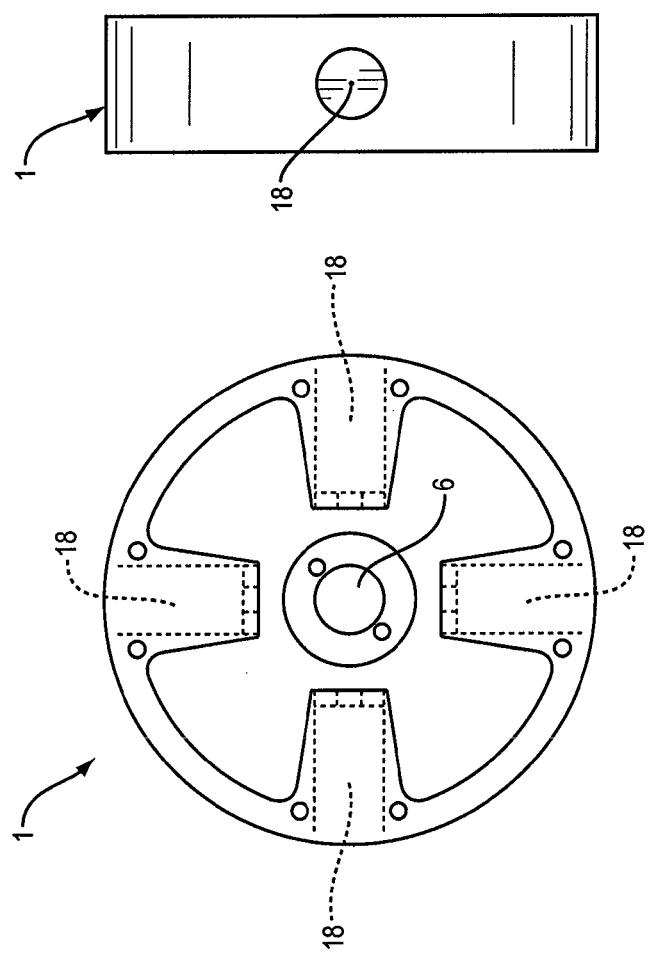

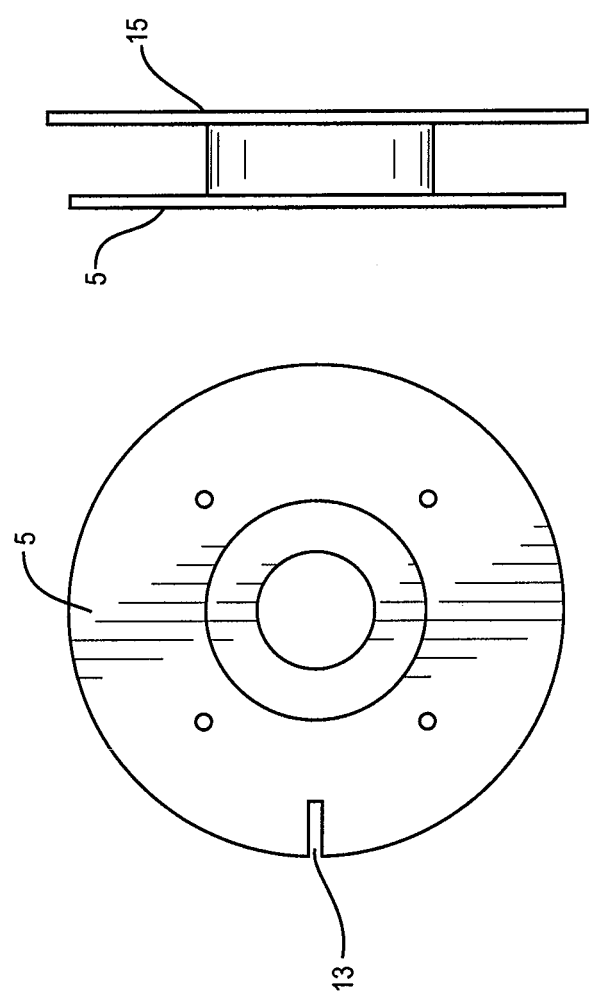

AUTOMATIC SONIC/ULTRASONIC DATA ACQUISITION DEVICE AND SYSTEM

CROSS-REFERENCE TO RELATED APPLICATION

This application claims priority of Provisional Patent Application 61/266,246 filed Dec. 3, 2009.

FIELD

This disclosure relates to the detection of faults in concrete structures using sound waves.

BACKGROUND

Measurements of the velocity that compressional and/or shear/Rayleigh waves propagate along and through concrete and impact echo thickness resonant frequencies have been used to evaluate the integrity and condition of PCCP (Prestressed Concrete Cylinder Pipe) and RCP (Reinforced Concrete Pipe). The equipment used to acquire the sonic/ultrasonic data is a hand held array of sensors and a projectile impact energy source. This system is quite versatile and efficient but cannot be made to operate easily with a remotely operated vehicle (ROV) necessary to evaluate smaller diameter pipes that an operator cannot enter.

SUMMARY

In general, featured herein is a device that is adapted to be moved through concrete pipe or across another concrete surface and automatically acquire sonic/ultrasonic time series data, to allow the evaluation of the integrity or condition of the pipe or concrete.

This disclosure features an automatic sonic/ultrasonic data acquisition device that is constructed and arranged to be moved across the surface of a concrete structure to collect data from the structure. The device has a frame, a plurality of wheels carried by the frame, one or more sensors carried by a wheel and constructed and arranged to contact the structure as the wheels roll along a surface of the structure, and an energy source for initiating compressional and/or shear waves in the structure that are sensed by the sensors.

There may be at least one sensor coupled to at least two of the wheels. The sensors may comprise pressure transducers. The pressure transducers may operate without a power supply, and may be piezoelectric sensors. The device may further comprise timing structure that causes two or more of the wheels to rotate in unison as the device is moved. The timing structure may comprise a sprocket on each of the two or more wheels and a timing chain that interconnects the sprockets. The device may further comprise additional devices that cause data from the pressure transducers to be transferred, for example to a storage device or a wireless transmitter. These additional devices may include wiring and a slip ring electrically coupled to the pressure transducers.

BRIEF DESCRIPTION OF DRAWINGS

FIGS. 1A and 1B are side and front views of a preferred embodiment of the automatic sonic/ultrasonic data acquisition device.

FIGS. 2A and 2B are front and top views of the wheel assembly for the preferred embodiment.

FIGS. 3A and 3B are front and side views of the laser photo interrupt plate mounted on the sprocket of the leading wheel of each device for the preferred embodiment.

DESCRIPTION OF EMBODIMENTS

Figure 1B:
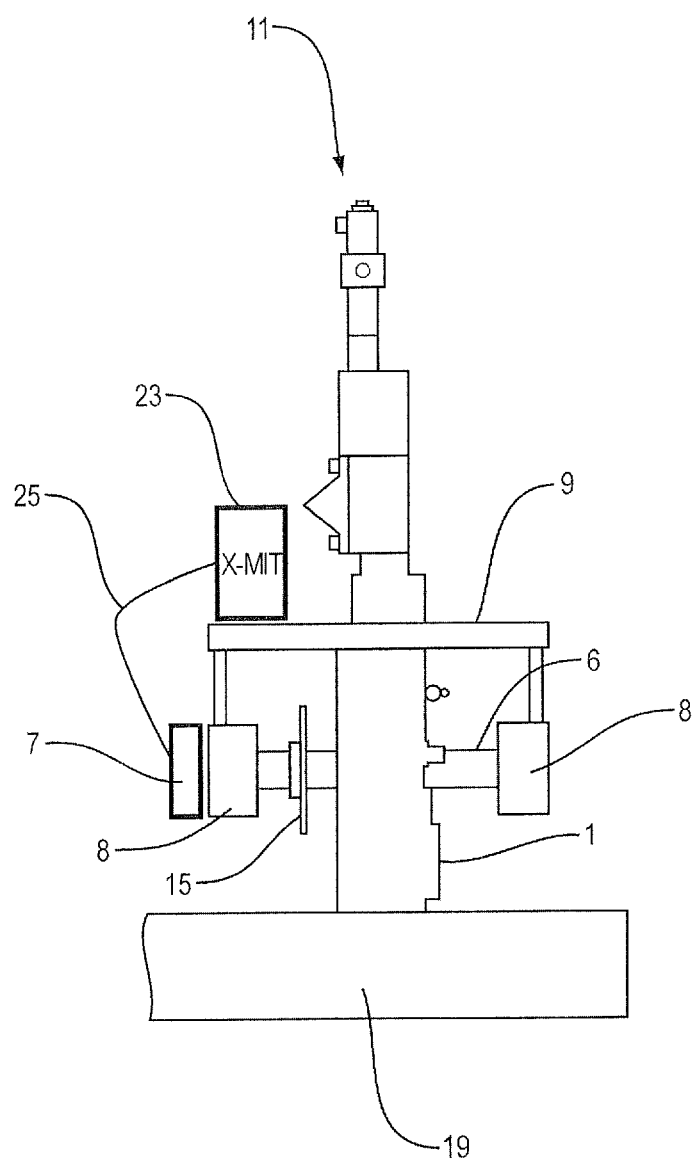

Disclosed herein is a device and system to automatically acquire sonic/ultrasonic time series data. A device is pushed or pulled along a surface of a reinforced concrete structure being tested, for example concrete pipe. The device includes two or more wheels that are coupled to a frame and roll along the surface of the structure being tested as the system is moved. The wheels are coupled such that they rotate in unison. Each wheel carries one or more pressure transducers; the coupling of the wheels ensures that one pressure sensor associated with each of the wheels contacts the underlying surface at the same moment. This ensures that each pressure transducer is sensing the same signal, but at different locations on the structure being tested. The device carries some means of initiating sonic or ultrasonic compressional and shear waves in the structure, typically via an impact source. The device also includes a timing system that initiates the waves at the proper time relative to the wheels' circumferential location such that the pressure sensors mounted on the wheels detect the waves.

The device further includes a means to carry the signals generated by the pressure transducers to electronics carried by the frame that either store the signals or transmit them to processing and storage located remotely from the system. Since the pressure transducers are mounted on rotating wheels, typically a slip ring is used to transmit the signals from the axle that carries the wheel to a stationary circuit that carries the signals either to a preamp and/or a transmitter. Alternatively, the device can carry memory to store the signals, or transmitters could be located on the structure that is rotated along with the wheels so that slip rings would not need to be used.

An embodiment of the device and system is shown in the drawings. Device 20 is comprised of an array of two or more (e.g., three) small diameter wheels 1 carried on frame 9. Frame 9 can be made in part from bar stock that defines longitudinal channels on the underside, to which the bearing blocks are mounted; this allows the wheels to be moved and positioned and spaced as desired along the length of the frame depending on the characteristics of the structure being tested. One or more of the wheels are equipped with one or more pressure transducers 2 that project slightly from the outer surface of the wheel. The wheels are coupled together so that they rotate in unison. With pressure sensors in multiple wheels, the system will automatically acquire sonic/ultrasonic nondestructive testing data at different pipe positions, to allow the evaluation of concrete pipe or other reinforced concrete structures 19.

The wheels are made to rotate in unison, thus keeping the pressure sensors 2 in the multiple wheels rotating in unison and thus contacting the concrete surface 19 in unison. This can be accomplished with a sprocket 15 mounted on the exterior of each wheel, and a chain drive 3 that interconnects the sprockets. The center wheel bearing block is spring mounted 4 to frame 9 so it can articulate up and down approximately 2 inches; this helps to keep all of the wheels in contact with the concrete surface while passing over ridges and valleys in the surface. The energy source 11 (e.g., a compressed gas operated pistol that fires a ball bearing) that generates the sonic/ultrasonic signal is activated by a laser photo interrupt (not shown) that is positioned such that it operates as slot 13 in the timing plate (disc 5) is moved past the interrupt. Disc 5 is coupled to only one of the wheels, as shown in FIGS. 3A and 3B. Disc 5 is coupled to the chain drive through sprocket 15 so that the interrupt activates when the sensors roll into position on the surface of the structure being tested. There could be more than one timing slot 13 if it was desirable to initiate more than one measurement per revolution of disc 5.

The pressure transducers (typically piezoelectric sensors that do not require power to operate) are mounted in cavities 18 in the wheels 1 with a rubber backing (not shown) that acoustically isolates the sensor from the rest of the system and applies approximately five to ten pounds of back pressure to push the sensor against the surface of the structure being tested. The wheels can have multiple cavities so that multiple sensors can be carried by each wheel. Four cavities 18 are depicted in FIG. 2. The wheels have a known circumference (in this case, two feet). This construction allows signals to be sensed at desired intervals along the structure. For example, with four equally spaced sensors per wheel, data will be captured every six inches along the device travel direction. Four timing slots 13 would be required in this case.

Figure 4:
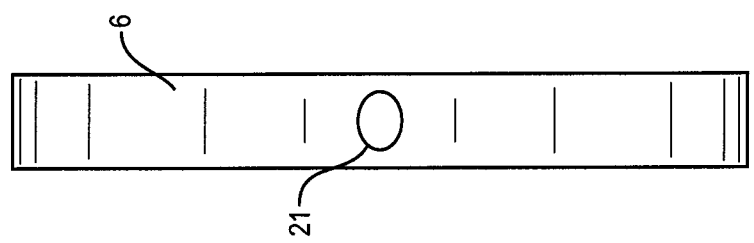
FIG. 4 shows the wheel axle that the wheel assembly, slip ring and bearings mount to for the preferred embodiment.
Figure 5:
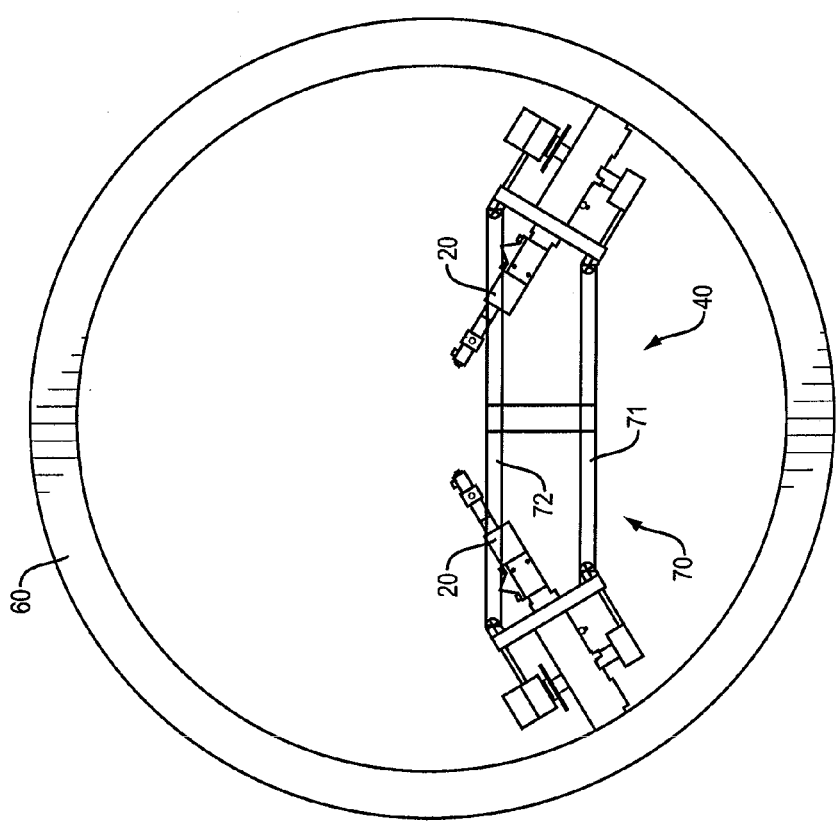
FIG. 5 shows a system comprising two of the devices of FIG. 1 mounted to an interconnection structure, located inside of a pipe being tested.

Sonic/ultrasonic signals recorded by the sensors are communicated by wiring that runs from the sensor through a radial hole 21 in the axle 6, that meets with a longitudinal hole that runs out to one end of the axle. See FIG. 4. This wiring terminates at a slip ring assembly 7 mounted on the outside of the bearing block assembly 8. The bearing block assembly houses axle needle bearings that allow the wheels to rotate easily and smoothly, and serves as a mounting point for the wheels to the frame 9. Wiring 25 connects slip ring 7 to on-board memory device and/or wireless transmitter 23. The collected data can then be analyzed to determine the quality of the concrete structure, in a manner known in the art. The battery power source carried by the device is not shown.
Operation to Test PCCP or RCP In system 40, FIG. 5, two, three-wheel acquisition devices 20 are mounted so that data can be acquired on different locations along the length of the pipe 60; for example with two devices 20 one can travel at the 4:00 o'clock pipe position and the other at the 8:00 o'clock pipe position. More than two devices 20 can be included if desired. Devices 20 operate simultaneously, preferably with the sensors' contact point six to twelve inches out of synchronization with each other with respect to the direction of travel of devices 20. Each wheel has a sprocket for chain drive 3 that keeps the sensors of each device synchronized so the sensors contact the wall of the pipe 60 simultaneously or in a predetermined pattern. When the sensors roll into place against the pipe, slot 13 allows a laser signal to pass, signaling, via a photoreceptor and a switch, the sonic/ultrasonic energy source 11 to initiate. Signals recorded by the pressure transducer sensors 2 are communicated by wires through the wheel axle 6 to a slip ring 7 at the end of the axle. The axles/wheels are kept in alignment with needle bearings mounted in bearing boxes 8 at each side of the wheel. Interconnection structure 70 holds two devices 20 in position so that they roll in unison along the inside of pipe. Changing the length of cross-members 71 and 72 of interconnect structure 70 allows the system to be used in different diameter pipes.

Figure 6:
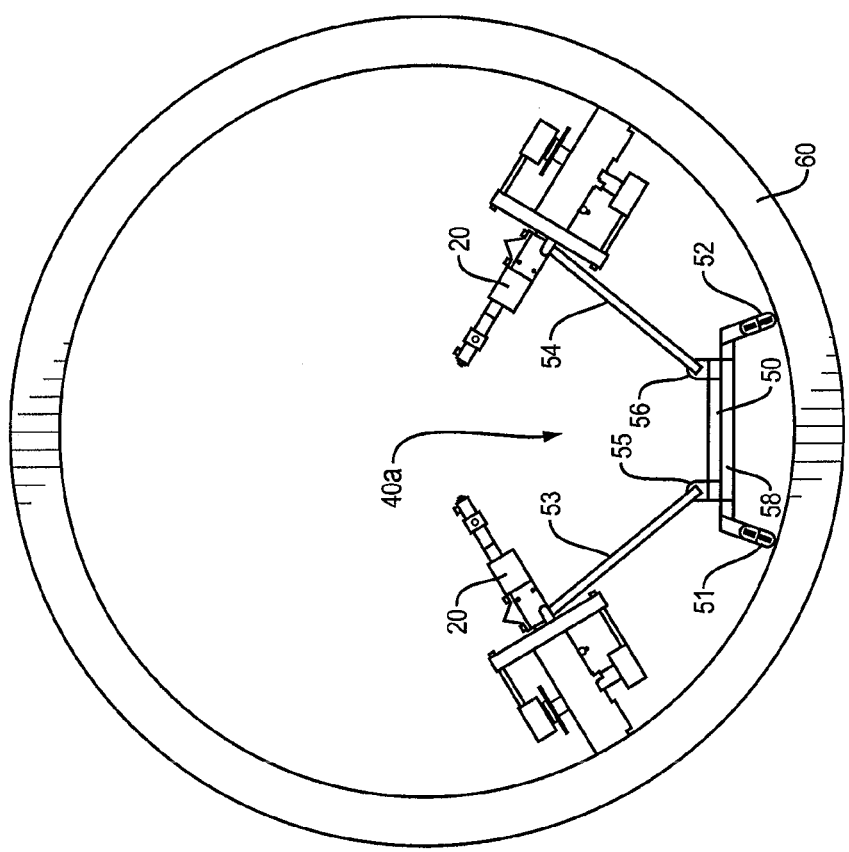
FIG. 6 shows an alternative system to that shown in FIG. 5, the system comprising two of the devices of FIG. 1 mounted to an articulating interconnection structure, located inside of a pipe being tested.

An alternative interconnect structure 50 of system 40a is shown in FIG. 6. Structure 50 carries wheels 51 and 52 so that it rolls along the inside of pipe 60. Arms 53 and 54 each carry one of the devices 20, and are pivotally connected to center support 58 of structure 50 at locations 55 and 56, respectively. This construction accomplishes an articulating structure that helps to accommodate different diameter pipes without the need to change the length of the cross-members.

What is claimed is:

1. An automatic sonic/ultrasonic data acquisition device that is constructed and arranged to be moved across the surface of a concrete structure, to collect data from the structure, comprising:
   a frame;
   a plurality of sensor wheels carried by the frame such that they roll along the surface as the device is moved along the surface of the concrete structure;
   one or more pressure transducers embedded in each wheel such that they each project slightly from the surface of the wheel at one particular circumferential location of the wheel, so that the pressure transducers momentarily contact the structure as the wheels roll along a surface of the structure, where the pressure transducers are operable to sense pressure without a power supply;
   a timing structure that causes the sensor wheels to rotate in unison as the device is moved across the surface of the structure such that one of the pressure transducers of each sensor wheel simultaneously contacts the surface of the structure;
   a projectile energy source that fires a projectile against the concrete structure so as to initiate compressional and/or shear waves in the structure that are sensed by the pressure transducers; and
   a projectile energy source timing mechanism that triggers the projectile energy source to fire the projectile when the pressure transducers are simultaneously in contact with the surface of the structure, such that such pressure transducers detect the compressional and/or shear waves that are initiated in the structure by the impact of the projectile.

2. The device of claim 1 in which the pressure transducers comprise piezoelectric sensors and the sensors are backed by a backing that acoustically isolates the sensor from the wheel and applies a back pressure to the sensor to push the sensor against the surface of the concrete structure.

3. The device of claim 1 in which the timing structure comprises a sprocket on each of the sensor wheels and a timing chain that interconnects the sprockets.

4. The device of claim 1 further comprising comprise wiring and a slip ring electrically coupled to the pressure transducers to cause data from the pressure transducers to be transferred out of the sensor wheels.

5. The device of claim 1 with multiple pressure transducers embedded in each sensor wheel such that they each project slightly from the surface of the wheel at evenly-spaced circumferential locations of the wheel.

6. An automatic sonic/ultrasonic data acquisition system that is constructed and arranged to move across the surface of a concrete structure, to collect data from the structure, comprising:
   (i) two or more data acquisition devices, each data acquisition device comprising:
      a frame;
      a plurality of sensor wheels carried by the frame such that they roll along the surface as the device is moved along the surface of the concrete structure;

one or more pressure transducers embedded in each wheel such that they each project slightly from the surface of the wheel at one particular circumferential location of the wheel, so that the pressure transducers momentarily contact the structure as the wheels roll along a surface of the structure, where the pressure transducers are operable to sense pressure without a power supply;

a timing structure that causes the sensor wheels to rotate in unison as the device is moved across the surface of the structure such that one of the pressure transducers of each sensor wheel simultaneously contacts the surface of the structure;

(ii) a projectile energy source that fires a projectile against the concrete structure so as to initiate compressional and/or shear waves in the structure that are sensed by the pressure transducers; and (iii) a projectile energy source timing mechanism that triggers the projectile energy source to fire the projectile when the pressure transducers are simultaneously in contact with the surface of the structure, such that such pressure transducers detect the compressional and/or shear waves that are initiated in the structure by the impact of the projectile; and (iv) an interconnection structure that interconnects the data acquisition devices so that the data acquisition devices move in unison across the surface.

7. The system of claim 6 in which the pressure transducers comprise piezoelectric sensors and the sensors are backed by a backing that acoustically isolates the sensor horn the wheel and applies a back pressure to the sensor to push the sensor against the surface of the concrete structure.

8. The system of claim 6 in which the timing structure comprises a sprocket on each of the sensor wheels and a timing chain that interconnects the sprockets.

9. The system of claim 6 with multiple pressure transducers embedded in each sensor wheel such that they each project slightly from the surface of the wheel at evenly-spaced circumferential locations of the wheel.

* * * * *